US006682904B1

United States Patent
Frost

(10) Patent No.: US 6,682,904 B1
(45) Date of Patent: Jan. 27, 2004

(54) SPECIFIC INHIBITORS OF HYALURONIDASE 2, AND METHODS OF IDENTIFYING AND USING SAME

(75) Inventor: Gregory I. Frost, Solana Beach, CA (US)

(73) Assignee: Deliatroph Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 10/222,032

(22) Filed: Aug. 15, 2002

(51) Int. Cl.[7] ............................. C12Q 1/34; C12Q 1/00; C12Q 1/02; C12N 9/26
(52) U.S. Cl. ............................. 435/18; 435/4; 435/29; 435/201
(58) Field of Search ............................. 435/18, 4, 29, 435/201

(56) References Cited

U.S. PATENT DOCUMENTS 6,001,356 A * 12/1999 Mikecz et al. ............ 424/144.1
6,123,938 A * 9/2000 Stern et al. ............... 424/94.62
6,572,855 B1 * 6/2003 Johnsson et al. ........... 435/201

* cited by examiner

Primary Examiner—Louise N. Leary
(74) Attorney, Agent, or Firm—Gray Cary Ware & Freidenrich LLP; Lisa A. Haile; Richard J. Imbra

(57) ABSTRACT

Methods for identifying a hyaluronidase 2 (HYAL2) specific inhibitor, which selectively inhibits HYAL2 activity, but does not substantially affect the activity of non-inflammatory hyaluronidases, are provided. Also provided are HYAL2 specific inhibitors obtained using such a method. In addition, methods for ameliorating an inflammatory disorder or vasculitis condition by specifically inhibiting HYAL2 is provided.

28 Claims, 2 Drawing Sheets

SPECIFIC INHIBITORS OF HYALURONIDASE 2, AND METHODS OF IDENTIFYING AND USING SAME

BACKGROUND OF THE INVENTION

1. Field of the Invention

The invention generally relates to hyaluronidase 2 (HYAL2) inhibition and, more specifically, to molecules that specifically inhibit HYAL2 activity, to methods of identifying HYAL2-specific inhibitors, and to methods for ameliorating a condition associated with the pro-inflammatory activity of HYAL2, including, for example, chronic inflammation or vasculitis, by specifically inhibiting HYAL2 activity and, therefore, HYAL2 mediated generation of pro-inflammatory and pro-angiogenic hyaluronan intermediate fragments.

2. Background Information

Inflammation and necrosis of blood vessels (vasculitis), including arteries, veins, and capillaries, can occur in connection with exposure to infectious agents, mechanical trauma, radiation, or toxins, and in association with immunological responses or disorders. In many cases, however, no etiology can be determined for a vasculitis (Rubin and Farber, "Pathology" 3d ed. (Lippincott-Raven 1999); pages 514–520).

Numerous vasculitis disorders have been identified, and have been classified based on the size of the blood vessels that primarily are affected, i.e., small vessel, medium vessel, or large vessel, or based on general similarities of the disorders, e.g hypersensitivity vasculitis, which includes serum sickness and some, but not all, other disorders that involve, at least in part, an undesirable immune response. Despite these attempted classifications of vasculitis disorders, however, there is considerable overlap of signs and symptoms associated with the vasculitis disorders in different classification groups, and, therefore, it has been difficult to prescribe general treatment protocols.

The occurrence of vasculitis has variously been attributed to an involvement of immune mechanisms and to viral infection. A potential involvement of immune mechanisms originally was based on the identification of immune complexes in serum sickness, which was one of the first human immunological disorders associated with vasculitis. However, evidence is lacking for a role of the immune response in most cases of vasculitis. Anti-neutrophil cytoplasmic antibodies (ANCA) have been identified in association with Wegener's granulomatosis and microscopic polyarteritis, which are small vessel vasculitis disorders. However, it is not clear whether the appearance of ANCA is causal for these disorders or merely an effect that is observable. In fact, the difficulty in classifying and treating vasculitis is due to a lack of understanding of the etiology of the disorder. Thus, a need exists to identify a general etiology of vasculitis such that methods for early diagnosis and prevention or treatment of this disorder can be developed. The present invention satisfies this need and provides additional advantages.

SUMMARY OF THE INVENTION

The present invention is based, in part, on the discovery that structurally related hyaluronidase polypeptides have opposing mechanisms of action, including pro-inflammatory or anti-inflammatory activity, such that broad spectrum hyaluronidase inhibitors can cause undesirable effects when administered to an individual. As disclosed herein, the use of agents that specifically inhibit hyaluronidase 2 (HYAL2), which has pro-inflammatory activity, provides a means to ameliorate pathologic conditions associated an undesirable inflammatory response due to generation of an intermediate hyaluronan catabolite by HYAL2.

Accordingly, the present invention relates to a method of identifying an agent that specifically inhibits HYAL2 activity, without substantially affecting the activity of non-inflammatory and anti-inflammatory hyaluronidases. Such a method can be performed, for example, by contacting HYAL2 and hyaluronan (HA) with a test agent, under conditions sufficient for HYAL2 activity, and detecting a decrease in HYAL2 activity. In the same reaction, or in a different reaction, which can be run in parallel, the activity of one or more non-inflammatory hyaluronidases such as HYAL1 or PH20 can be determined to confirm that an agent that inhibits HYAL2 activity has substantially less, if any, effect on the non-inflammatory (or anti-inflammatory) hyaluronidase(s) and, therefore, is a specific inhibitor of HYAL2.

A screening assay of the invention can be performed using cells that express HYAL2, either naturally or due to introduction of a HYAL2 encoding transgene, or using a detergent extract of such cells, including the membrane fraction, which contains the associated HYAL2. Where a cell that is genetically modified to express HYAL2 is used, or a detergent extract of such a cell, the transgene, which encodes HYAL2, can be transiently contained in the cell, or can be stably maintained by integration into the cell genome. Such a stably transfected cell can provide a standardized source of membrane associated HYAL2 useful for performing a screening assay of the invention. A screening assay of the invention also can be practiced using HYAL2 associated with a synthetic membrane, for example, a lipid bilayer or a unilamellar or multilamellar vesicle such as a liposome.

A decrease in HYAL2 activity can be detected directly by measuring a decrease in the amount or rate of generation of the pro-inflammatory 20 kDa intermediate HA catabolite following addition of the test agent, or can be detected indirectly by detecting decreased expression of a reporter gene regulated from a chemokine promoter, which exhibits induced expression in the presence of the 20 kDa intermediate. Such a reporter gene includes the chemokine promoter, for example, a RANTES, promoter, operatively linked to a nucleotide sequence encoding a detectable polypeptide as an enzyme; a fluorescent or luminescent polypeptide; a ligand (or receptor) that specifically binds a particular receptor (or ligand); or the like.

An agent that specifically inhibits HYAL2 activity can be any type of molecule, including, for example, a peptide (or polypeptide), a polynucleotide, a peptidomimetic, a peptoid, or a small organic molecule. For example, the agent can be an anti-HYAL2 antibody, or a HYAL2 binding fragment of said antibody. It will be recognized that the screening assays of the invention are readily adaptable to a high throughput format. As such, the methods allow for the screening of large numbers of test agents in parallel, and further allow for control reactions to be run in parallel, for example, reactions containing non-inflammatory or anti-inflammatory hyaluronidases, thus providing internal controls useful for confirming that an agent specifically inhibits HYAL2 activity without substantially affecting the activity of hyaluronidases that are not pro-inflammatory.

The present invention further relates to a HYAL2 specific inhibitor identified using such a screening assay. The HYAL2 specific inhibitor can be useful as a purified reagent, for example, as a material to be added to cells in culture to specifically inhibit HYAL2 activity, thus providing a standard for a screening assay to identify agents that can specifically inhibit HYAL2 activity, or can be formulated as a composition, which, for example, can be in a form suitable for administration to a subject, including a vertebrate subject such as a mammal, particularly a human. Such a composition containing a HYAL2 specific inhibitor can be useful for treating an inflammatory disorder associated with HYAL2 activity, for example, a vasculitis, by reducing or inhibiting HYAL2 activity, thereby reducing the generation of the pro-inflammatory 20 kDa intermediate HA breakdown product. Accordingly, the present invention provides a medicament useful for treating a subject having such an inflammatory disorder.

The present invention also relates to a method of ameliorating an inflammatory condition associated with HYAL2 mediated generation of a 20 kDa intermediate HA breakdown product in a subject. Such a method can be performed, for example, by administering a HYAL2 specific inhibitor to the subject, whereby HYAL2 activity is reduced or inhibited, thereby ameliorating the inflammatory condition in the subject. In one embodiment, the HYAL2 specific inhibitor is a HYAL2 specific inhibitor identified according to a screening assay of the invention, for example, an anti-HYAL2 antibody or a HYAL2 binding fragment of said antibody, which specifically binds to and inhibits the activity of HYAL2 without affecting non-inflammatory or anti-inflammatory hyaluronidases, or can be a polynucleotide, peptide, small organic molecule, or the like having HYAL2 specific inhibitory activity. In another embodiment, the HYAL2 specific inhibitor is a polynucleotide that modulates HYAL2 gene expression, for example, an antisense molecule, a ribozyme, a triplexing agent, or an RNA molecule that mediates RNA interference.

The present invention also relates to methods for treating a vasculitis associated with HYAL2 activity in a subject, or a predisposition to such a vasculitis, and further relates to methods of ameliorating such a vasculitis, including preventing or reducing the severity of the vasculitis in a subject. Accordingly, in one embodiment, the present invention relates to a method of ameliorating a vasculitis in a subject, wherein the vasculitis is associated with an elevated (greater than normal) level in the blood of a hyaluronan (HA) catabolite having a molecular mass of about 20 kiloDaltons (kDa) or greater. Such a method can be performed, for example, by inhibiting HYAL2 activity in the subject, without substantially affecting the activity of anti-inflammatory hyaluronidases such as HYAL1, which can degrade pro-inflammatory HA catabolites.

In one aspect of a method of ameliorating a vasculitis in a subject, HYAL2 activity is inhibited in a subject having or predisposed to the vasculitis by administering a HYAL2 specific inhibitor. The inhibitor can be a monoclonal antibody or a small molecule inhibitor. The inhibitor also can be any molecule capable of specifically inhibiting HYAL2, for example, an antibody or other peptide or polypeptide; a small organic molecule such as a peptidomimetic; or a polynucleotide. For example, a specific inhibitor of HYAL2 activity can be a monoclonal antibody that selectively binds HYAL2, but not other hyaluronidases, particularly not anti-inflammatory hyaluronidases. A HYAL2 binding fragment of such a monoclonal antibody, for example, an Fab or F(ab')2 fragment, can be particularly useful for specifically inhibiting HYAL2 activity in vivo because such a fragment does not, for example, stimulate immunoeffector functions such as complement fixation.

In one embodiment, a polynucleotide useful as a specific inhibitor of HYAL2 can be a nucleic acid molecule that is complementary to a naturally occurring polynucleotide encoding HYAL2, including DNA or RNA, thereby reducing or inhibiting the production of HYAL2 polypeptides in a subject. Such nucleic acid molecules can be, for example, antisense nucleic acid molecules, ribozymes, triplexing agents, or RNA molecules that mediate RNA interference. In another embodiment, the nucleic acid molecule for inhibiting HYAL2 activity is a functional nucleic acid that specifically binds to and inhibits HYAL2 activity.

A method of the invention provides a means to prevent or reduce the severity of a vasculitis associated with an elevated level in the blood of a hyaluronan catabolite having a molecular mass of about 20 kDa in a subject by inhibiting HYAL2 activity, thereby reducing or inhibiting generation of the pro-inflammatory 20 kDa HA intermediate degradation product. The vasculitis can be a small vessel vasculitis, which includes vasculitis of small arterioles, capillaries and post-capillary venules; or medium vessel vasculitis, which includes vasculitis of muscular arteries of about 0.2 to 2 mm diameter; or can be a large vessel vasculitis, which includes vasculitis of elastic arteries. For example, the vasculitis can be a vasculitis of the polyarteritis nodosa group of systemic necrotizing vasculitis such as polyarteritis nodosa, which affects medium sized and smaller muscular arteries and, occasionally, larger arteries; or allergic angiitis and granulomatosis (Churg-Strauss variant), which affects small and medium sized arteries, arterioles and veins. The vasculitis also can be a hypersensitivity angiitis, for example, serum sickness, Henoch-Schonlein purpura, vasculitis associated with a connective tissue disorder, or vasculitis associated with essential mixed cryogloulinemia. In addition, the vasculitis can be Wegener granulomatosis, which is a systemic necrotizing vasculitis that generally involves small arteries and veins, particularly in the respiratory tract, kidney and spleen. The vasculitis also can be a giant cell arteritis, for example, temporal arteritis or Takayasu arteritis, or can be Kawasaki disease, thromboangiitis obliterans, or Behcet disease. A subject suitable for treatment according to a method of the invention is one having a vasculitis or a predisposition to a vasculitis due to generation of intermediate HA catabolites by HYAL2 can be identified, for example, by detecting a lower than elevated HYAL2 activity in a blood plasma or serum sample or by detecting the pro-inflammatory HA intermediate, which has a molecular mass of about 20 kDa.

BRIEF DESCRIPTION OF THE DRAWINGS

As shown in FIG. 1(a), a sample of high molecular weight hyaluronan substrate is added to the microtiter assay with the test inhibitor plus HYAL2 enzyme. In the control well Substrate only or Substrate with inhibitor is added. In the positive control well, Substrate with HYAL2 enzyme is added. In the test sample, Substrate with HYAL2 and Inhibitor is added. In FIG. 1(b) the enzyme is activated by acidic pH or by mixing in activated enzyme and is allowed to digest substrate. In FIG. 1(c), denatured albumin solution is added and a turbid reaction is allowed to develop. As shown in FIG. 1(d), negative control wells lacking enzyme will become turbid due to the interaction of denatured albumin with high molecular weight hyaluronan. This turbid reaction may be measured optimally at 540 nm in a microtiter plate reader. In sample wells containing active enzyme with substrate, a turbid reaction will not develop due to depolymerization of the Hyaluronan substrate. In sample wells containing an active inhibitor of HYAL2 however, the sample will develop turbidity in proportion to the degree of inhibition. The amount of enzyme added should be diluted appropriately to permit near complete reduction of turbidity such that the presence of an inhibitor will be rapidly detected.

DETAILED DESCRIPTION OF THE INVENTION

Figure 1:
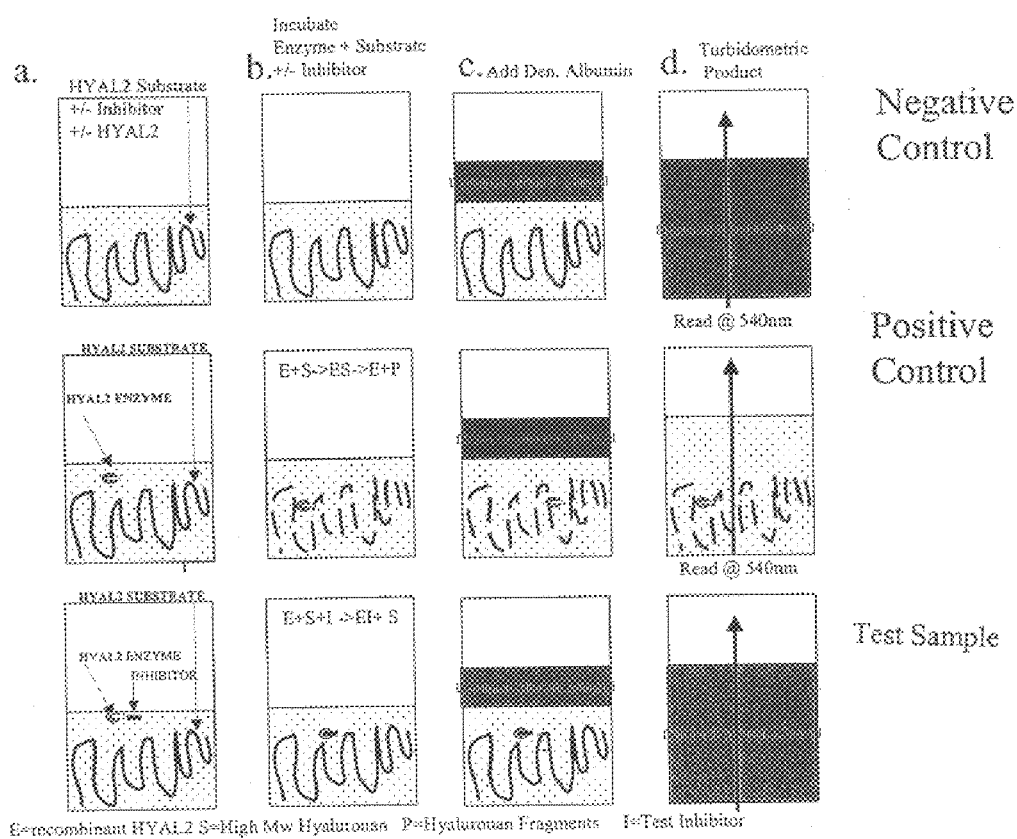
FIG. 1 shows a description of the turbidometric assay adopted to microtiter format for high throughput screening of HYAL2 candidate inhibitors.
Figure 2:
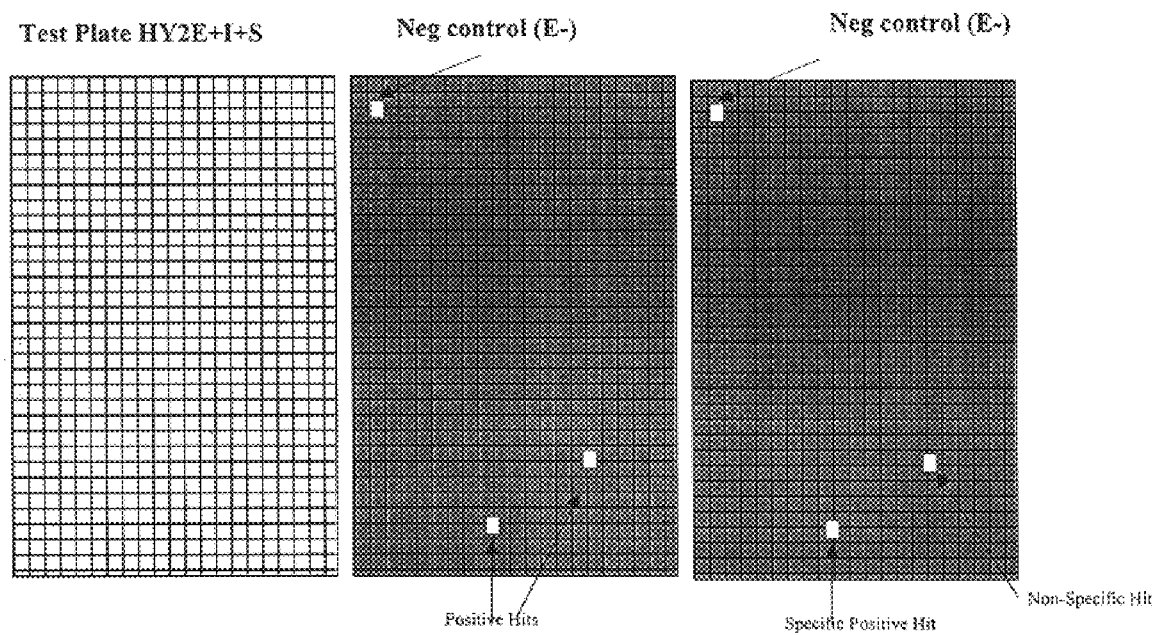
FIG. 2 shows that test inhibitors can be compared either in series or parallel with non non-inflammatory hyaluronidases to identify specific inhibitors of HYAL2 that do not interfere with non-inflammatory enzymes that may be beneficial to the resolution of inflammatory conditions associated with HA fragments.

The present invention is based, in part, on the determination that hyaluronidase 2 (HYAL2) activity in a subject allows an accumulation of an intermediate (20 kiloDalton; 20 kDa) breakdown product of hyaluronan (HA), which is a pro-angiogenic and pro-inflammatory product that generates a deleterious inflammatory reaction resulting in various disparate but related disorders, and that inhibition of HYAL2 activity, without also inhibiting the activity on non-inflammatory or anti-inflammatory hyaluronidases, allows amelioration of an undesirable inflammatory response due to HYAL2 mediated generation of the pro-inflammatory intermediate HA catabolite. Accordingly, the present invention provides screening assays for identifying HYAL2 specific inhibitors, HYAL2 specific inhibitors identified using such assays, and methods of using HYAL2 specific inhibitors to ameliorate an inflammatory response. The HYAL2 specific inhibitors of the present invention provide a significant advantage over previously described broad spectrum hyaluronidase inhibitors in that the HYAL2 specific inhibitors do not substantially affect the activity of hyaluronidases that, for example, breakdown the pro-inflammatory 20 kDa intermediate HA catabolite to non-inflammatory oligosaccharides.

Angiogenesis is a fundamental process by which new blood vessels are formed. Although angiogenesis is rare in adult mammals under normal physiological conditions it can occur, for example, during with wound healing, and ceases upon completion of the healing process. However, angiogenesis also occurs in association with various pathologic conditions, including in cancer, and in association with chronic inflammatory conditions. The inhibitory controls that limit angiogenesis during normal processes such as wound healing often fail in pathologic conditions, and angiogenesis persists.

Angiogenesis begins with an inflammatory phase that is characterized by dilated and permeable vessels. This early inflammatory response is followed by a degradative step, whereby the basement membrane of the endothelium is degraded through the action of a variety of matrix degrading enzymes. Matrix degradation is followed by migration of capillary endothelial cells towards angiogenic stimuli, resulting in the endothelial cells migrating from the vascular wall through perivascular connective tissue and into tissue parenchyma. Proliferation of endothelial cells behind the leading front of migrating endothelial cells then occurs, continuing the angiogenesis process.

A variety of soluble polypeptides and other factors are involved in the promotion of endothelial cell proliferation during angiogenesis. For example, the vascular endothelial growth factor (VEGF) and angiopoietin protein families are endothelial cell-specific mitogens and growth factors that are critical for the organization and development of vasculature during fetal development and wound healing. Other factors such as the fibroblast growth factor (FGF) family are more pleiotropic and also can play a role in angiogenesis.

Structural components of the extracellular matrix also are involved in the modulation of endothelial cell function. In addition, degradation products of basement membrane, stroma, and proteins of the clotting cascade, can variously reinforce or inhibit the process of neovascularization. In many cases, the ability of a matrix degradation product to effect angiogenesis is not found in the parent molecule, but is unique to the degradation product.

Glycosaminoglycans are structural components of the extracellular matrix that are extensively modified during angiogenesis. Sulfated glycosaminoglycans such as heparan sulfate can function both as mature components of the endothelial basement membrane and as reservoirs for critical growth factors such as VEGF and basic FGF, which are released upon digestion of the matrix by the action of heparanases. Other glycosaminoglycans such as hyaluronan (HA) are present during inflammation and angiogenesis, and are removed at the end of tissue remodeling. HA is a high molecular weight linear glycosaminoglycan that inhibits endothelial cell migration and proliferation when present in its native state, but elicits a robust induction of angiogenesis when it is degraded to low molecular weight fragments (see, for example, Folkman, Nat. Med. 1:27–31, 1995; Hulett et al., Nat. Med. 5:803–809, 1999). Treatment of bovine aortic endothelial cells with hyaluronidase derived HA fragments of about 3 to 10 disaccharides in length induces endothelial cell proliferation, tube formation and tyrosine kinase activity (Folkman, supra, 1995), and the onset of angiogenesis in vivo is preceded by a decrease in hyaluronan content and size.

HA is the only non-sulfated glycosaminoglycan, and is prominent in connective tissue, cartilage, and synovial fluid (Laurent et al., Ann. Rheum. Dis. 54:429–432, 1995), and is present under condition where rapid tissue turnover is occurring such as during embryonic development and during wound healing (Ruggiero et al., J. Dent. Res. 66:1283–1287, 1987). HA is synthesized by a family of HA synthases (HAS), including HAS1 HAS2 and HAS3, which incorporate UDP-N-acetylglucosamine and UDP-glucuronic acid into the high molecular weight polymer. The cellular location of the three HA synthases have not been established, though they may reside in the plasma membrane (Klewes et al., Biochem. J. 791–795, 1993).

Inactivation of the HAS2 gene in the mammalian genome results in severe vascular defects, and results in loss of viability by embryonic day 9.5 (E 9.5). HAS2 null embryos fail to form an endocardial cushion, and possess little vasculature as determined by PECAM staining (Camenisch et al., J. Clin. Invest. 106:335–336, 2000). Beyond the structural defects in the production of vasculature, endothelial-mesenchymal conversion is defective, but can be rescued by constitutive ras signaling or through the addition of exogenous HA at nanogram levels.

HA fragments can elicit cell-type specific responses. For example, in macrophages, HA fragments (<400 kDa) can up-regulate chemokine expression and nitric oxide synthase, without requiring new protein synthesis. This induction of immediate early response genes utilizes an NF-κB pathway independent of the LPS receptor, CD14 (Noble et al., J. Exp. Med. 183:2373–2378, 1996; McKee et al., J. Clin. Invest. 98:2403–2413, 1996). Sonication of high molecular weight HA (>6,000 kDa), which lacks any signaling capacity, to lower molecular weight fragments (<400 kDa) is sufficient to induce the HA chemokine response. This activation can be partially blocked with function perturbing anti-CD44 monoclonal antibodies or by the addition of high molecular weight HA.

Hyaluronidases are the primary enzymes involved in HA degradation. The vertebrate hyaluronidases (E.C 3.1.25) constitute a family of β,1–4 endoglucosaminidases that degrade HA and chondroitin sulfates (Kreil, *Protein Sci.* 4:1666–1669, 1995; Frost et al., *Trends Glycosci. Glycotechnol.* 8:407–421, 1996, each of which is incorporated herein by reference). These enzymes initially were grouped into two classes—those active at neutral pH, for example, the sperm-associated PH20 (Primakoff et al., *J. Cell Biol.* 101:2239–2244, 1985; Lin et al., *J. Cell Biol.* 125:1157–1163, 1994, each of which is incorporated herein by reference), and those with an acid pH optimum, including those present in extracts of liver, kidney, lung, brain, skin, placenta, macrophages, and fibroblasts, and in urine and human plasma (see, for example, Fiszer-Szafarz et al., *Acta Biochim. Pol.* 42:31–33, 1995; Thet et al., *Biochem. Biophys. Res. Comm.* 117:71–77, 1983; Goggins et al., *J. Histochem. Cytochem.* 16:688–692, 1968; Longaker et al., *Ann. Surg.* 213:292–296, 1991; DeSaleui and Pigman, *Arch. Biochem. Biophys.* 120:60–67, 1967, each of which is incorporated herein by reference). Although initial attempts to isolate these somatic hyaluronidases were met with limited success because of difficulties in stabilizing the purified proteins and their remarkably high specific activity, cDNA molecules encoding human and mouse hyaluronidases have been cloned (Frost et al., *Biochem. Biophys. Res. Comm.* 236:10–15, 1997, which is incorporated herein by reference), and a family of six homologous enzymes in the human and mouse genomes has been identified (Csoka et al., *Matrix Biol.* 20:499–508, 2001, which is incorporated herein by reference).

The sperm hyaluronidase, PH20, is the most thoroughly characterized of the hyaluronidase enzymes in mammalian species and is present at high levels of activity in testes extracts. PH20 is a glycosyl phosphatidylinositol-(GPI) anchored enzyme (Thaler and Cardullo, *Biochemistry* 34:7788–7795, 1995). The nucleotide sequence encoding PH20 has been determined, and the PH20 gene has been localized to chromosome 7q31 in humans (Jones et al., *Genomics* 29:796–800, 1995). PH20 expression is highest in the testes, and also is found in low levels in tumor cells and as well as microvascular endothelium (Mohamadzedeh et al., *J. Clin. Invest.* 1010:97–108, 1998).

PH20, which is normally bound to the plasma membrane through its GPI anchor, can be distinguished enzymatically by its broad pH optimum, as compared to other mammalian hyaluronidases, which display a sharp optima at pH 3.8 to 4.0. PH20 shares sequence homology with several venom hyaluronidases within the first 300 amino acids. Site-directed mutagenesis and deletion mapping has refined the catalytic domain of PH20 to the N-terminal domain within the first 300 amino acids (Arming et al., *Eur. J. Biochem.* 247:810–814, 1997, which is incorporated herein by reference).

Hyaluronidase 1 (HYAL1; also called LUCA1) is an acid-active HA-degrading activity was first identified in human plasma (Spicer et al., *J. Biol. Chem.* 272:8957–8961, 1997). Purification of the major hyaluronidase activity from human plasma led to the cloning of HYAL1/LUCA1 (Frost et al., supra, 1997). Human HYAL1 is encoded by a cDNA having a nucleotide sequence as set forth in GenBank Acc. No. U96078, and has an amino acid sequence as set forth in GenBank Acc. No. AAD04190, each of which is incorporated herein by reference; mouse HYAL1 is encoded by a cDNA having a nucleotide sequence as set forth in GenBank Acc. No. AF011567, and has an amino acid sequence as set forth in GenBank Acc. No. AAC15949, each of which is incorporated herein by reference (see, also, Frost et al., supra, 1997).

HYAL1 displays lipophilic properties in TRITON-X114 detergent that are resistant to phospholipase-C. HYAL1 is synthesized primarily in the liver, kidney, and heart, and in differentiated epithelium, where its expression is regulated by extracellular calcium. Recombinant HYAL1/LUCA1 is exclusively secreted and accumulates in the conditioned media of overexpressing HEK-293 cells. Paradoxically, HYAL1 possesses a strictly acidic pH optimum for enzyme activity in vitro. HYAL1 has substrate and size specificity identical to that of PH20, and degrades hyaluronan and chondroitin sulfate A/C to the tetrasaccharide, and only under acidic conditions (pH<4.5). The highest levels of HYAL1 activity are found in human plasma and urine, and it also is found intracellularly in some tissues such as the liver, where it is endoproteolytically processed within the carboxy terminus.

HYAL1 is removed from the circulation by a receptor mediated process into sinusoidal endothelial cells. Similarly, HA also requires receptor mediated endocytosis for degradation in the sinusoidal liver endothelium by HARLEC (Zhou et al., *J. Biol. Chem.* 275:37733–37741, 2000 As a recycling receptor, HARLEC requires dissociation of ligand in the endosomes for receptor recycling to ensue. Intermediate sized fragments of HA accumulate in endosomal compartments, thereby preventing dissociation of HARLEC and its ligand. Politz et al. (*Biochem. J.* 362:155–164, 2002) describe a family of two proteins, stabilin-1 and stabilin-2, which likely function as recycling receptors in sinusoidal endothelium and activated macrophages. Thus, in the absence of HYAL1, the recycling capacity of the HA receptor is compromised and becomes limited in its capacity to endocytose HA.

Karyotypic analysis of 16 SCLC cell lines identified deletions over chromosome 3p 14–23 (Whang-Peng et al., *Cancer Genet. Cytogenet.* 6:119–134, 1982). This region includes at least 3 regions that contain putative tumor suppressor genes, including several candidate tumor suppressor genes at 3p21.3 (Kok et al., *Adv. Cancer Res.* 71:27–92, 1997). A 30 kb deletion of the chromosome 3p21.3 region containing the HYAL1 gene also was identified in a SCLC cell line (Latif et al., *Hum. Genet.* 99:334–341, 1997), suggesting HYAL1 can act as a tumor suppressor gene. Hemizygosity over the candidate tumor suppressor gene locus on 3p21.3 also was reported for head and neck squamous cell carcinomas (Buchhagen et al., *Proc. Natl. Acad. Sci., USA* 89:10877–10881, 1992).

Cloning of the human plasma hyaluronidase, HYAL 1, led to the examination of the human EST database and the identification of a second somatic tissue hyaluronidase, termed HYAL2 (Lepperdinger et al., *J. Biol. Chem.* 273:22466–22470, 1998; see, also, U.S. Pat. No. 5,958,750, each of which is incorporated herein by reference; see, also,). The HYAL2 gene resides immediately centromeric to HYAL1 on human chromosome 3p21.3. HYAL2, like HYAL1, is an active-acid hyaluronidase, but, unlike HYAL1, does not digest chondroitin sulfates and digests HA only to an intermediate catabolite having an apparent molecular mass of approximately 20 kDa. The 20 kDa intermediate breakdown product has pro-inflammatory and pro-angiogenic activity. Although HYAL2 has been identified in lysosomes, it is anchored to the plasma membrane via a GPI anchor, and functions as the jaagsiekte sheep retrovirus receptor. HYAL2 is expressed in all tissues except the adult brain.

The murine HYAL2 gene is adjacent to the HYALL gene on mouse chromosome 9, between markers D9Mit183 and D9Mit17, placing HYAL2 between mouse dystroglycan and transferrin (Strobl et al., *Genomics* 53:214–219, 1998). Murine HYAL2 is expressed early in the brain, with highest expression at E10 and no expression by P30. This silencing correlates with the hypermethylation of a CpG island upstream of the HYAL2 gene. Mice null for the HYAL2 gene die early in gestation (E9), and have vascular defects similar to those found in HAS2 knockout mice.

HYAL2 is exemplified herein by a human HYAL2 polypeptide having an amino acid sequence as set forth as SEQ ID NO:2, which is encoded by SEQ ID NO:1 (U.S. Pat. No. 5,958,750). However, it will be recognized that the methods of the invention can be practiced using any HYAL2, including, for example, mouse HYAL2 (Chang, BMC *Cell Biol.* 3:8, 2002; GenBank Acc. No. AF422177, each of which is incorporated herein by reference); ovine HYAL2 (Dirks et al., *J. Virol.* 76:2141–2149, 2002; GenBank Acc. No. AF411974, each of which is incorporated herein by reference); bovine HYAL2 (Dirks et al., supra, 2002; GenBank Acc. No. AF411973, each of which is incorporated herein by reference), or any other HYAL2 such as those identified by a search on the world wide web at the URL "ncbi.nlm.nih.gov" using the search term "HYAL2". Thus, an antisense HYAL2 molecule can be designed, for example, based on SEQ ID NO:1, which encodes human HYAL2, and can be examined for the ability to specifically inhibit HYAL2 activity, such an antisense molecule being useful for ameliorating pathologic condition or an undesirable inflammatory response as disclosed herein.

Broad spectrum hyaluronidase inhibitors have been used to demonstrate a role of hyaluronidases in pathologies such as cancers and inflammatory disorders, and in an effort to treat such pathologic conditions (see, for example, Novak et al., *Cancer Res.* 59:6246–6250, 1999; Enegd et al., *Neurosurgery* 50:1311–1318, 2002). Broad spectrum hyaluronidase inhibitors are exemplified by flavonoids, including flavonoid aglycones such as apigenin, luteolin, and kaempferol, and the god-type ellagitannin (Kuppusamy and Das, *Experientia* 47:1196–1200, 1991; Panes et al., *Microcirculation* 3:279–286, 1996; Primakoff and Overstreet, *Biol. Reprod.* 56:1383–1389, 1997; Pessini et al., *Toxicon* 39:1495–1504, 2001; U.S. Pat. No. 5,843,911; WO 01/85191). Unfortunately, the use of broad spectrum hyaluronidase inhibitors to treat an inflammatory disorder provides the disadvantage that non-inflammatory and anti-inflammatory hyaluronidases such as HYAL1, which degrades the pro-inflammatory intermediate 20 kDa HA catabolite to non-inflammatory oligosaccharides, also are inhibited, thus allowing any of the pro-inflammatory HA catabolite that may be present, or that may be generated due to breakdown of high molecular HA by reactive oxygen species or other agents other than HYAL2 to remain in the subject, thereby prolonging the inflammatory response.

Accordingly, the present invention provides screening assays useful for identifying agents that specifically inhibit the activity of a pro-inflammatory hyaluronidase such as HYAL2. As disclosed herein, agents that specifically inhibit HYAL2 activity, for example, without substantially affecting the activity of non-inflammatory or anti-inflammatory hyaluronidases, can be used as therapeutics for treating a subject having an inflammatory condition due to generation of the 20 kDa intermediate HA breakdown product, a cancer associated with increased HYAL2 activity, and the like. Such HYAL2 specific inhibitors provide a distinct advantage over the use of broad spectrum hyaluronidase inhibitors in that the HYAL2 specific inhibitors do not substantially affect the activity of hyaluronidases that have anti-inflammatory activity. Accordingly, the present invention provides methods for identifying an agent that specifically inhibits HYAL2 activity, without substantially affecting the activity of non-inflammatory or anti-inflammatory hyaluronidases.

The term "pro-inflammatory", "non-inflammatory", or "anti-inflammatory", when used in reference to a hyaluronidase, is used herein with respect to the HA catabolites generated by the hyaluronidase. Thus, HYAL2 is referred to as a "pro-inflammatory" hyaluronidase because it breaks down high molecular weight HA to an intermediate product that has a molecular weight of about 20 kDa and that induces an inflammatory response in a vertebrate subject such as a human. In comparison, HYAL1 is referred to as an "anti-inflammatory" hyaluronidase because it degrades the pro-inflammatory 20 kDa intermediate to low molecular weight oligosaccharides that do not stimulate an inflammatory response.

HYAL2 activity generally requires that the hyaluronidase is membrane bound. As such, a screening assay of the invention can be performed using cells that express HYAL2, either naturally or due to introduction of a HYAL2 encoding transgene, or using a detergent extract of such cells, including the membrane fraction, which contains the associated HYAL2. Where a cell that is genetically modified to express HYAL2 is used, or a detergent extract of such a cell, the transgene, which encodes HYAL2, can be transiently contained in the cell, or can be stably maintained by integration into the cell genome. Such a stably transfected cell can provide a standardized source of membrane associated HYAL2 useful for performing a screening assay of the invention. A screening assay of the invention also can be practiced using HYAL2 associated with a synthetic membrane, for example, a lipid bilayer or a unilamellar or multilamellar vesicle such as a liposome.

A polynucleotide encoding HYAL2, for example, a polynucleotide encoding human HYAL2 (SEQ ID NO:1), generally is contained in a vector, particularly an expression vector, which can contain, in addition to the polynucleotide, regulatory elements useful for expressing the polynucleotide and, where the polynucleotide encodes a peptide, for expressing the encoded peptide in a particular cell. An expression vector can contain the expression elements necessary to achieve, for example, sustained transcription of the encoding polynucleotide, or the regulatory elements can be operatively linked to the polynucleotide prior to its being cloned into the vector. As disclosed herein, an expression vector also can be used to introduce a reporter gene into a cell to be used in a screening assay of the invention, wherein the reporter gene includes a regulatory element that is responsive to the presence in the cell of the 20 kDa intermediate HA catabolite (e.g., a chemokine promoter such as a RANTES, MIP1, MIP2, or inducing nitric oxide synthase (iNos) promoter) operatively linked to a nucleotide sequence encoding a detectable polynucleotide or polypeptide (e.g., a fluorescent polypeptide, a luminescent polypeptide, or an enzyme).

An expression vector (or the polynucleotide) generally contains or encodes a promoter sequence, which can provide constitutive or, if desired, inducible or tissue specific or developmental stage specific expression of the encoding polynucleotide, a poly-A recognition sequence, and a ribosome recognition site or internal ribosome entry site, or other regulatory elements such as an enhancer, which can be tissue specific. The vector also can contain elements required for replication in a prokaryotic or eukaryotic host system or both, as desired. A polynucleotide, which can be contained in a vector, can be introduced into a cell by any of a variety of methods known in the art (Sambrook et al., *Molecular Cloning: A laboratory manual* (Cold Spring Harbor Laboratory Press 1989); Ausubel et al., *Current Protocols in Molecular Biology*, John Wiley and Sons, Baltimore, Md. (1987, and supplements through 1995), each of which is incorporated herein by reference). Such methods include, for example, transfection, lipofection, microinjection, electroporation and, with viral vectors, infection; and can include the use of liposomes, microemulsions or the like, which can facilitate introduction of the polynucleotide into the cell and can protect the polynucleotide from degradation prior to its introduction into the cell. The selection of a particular method will depend, for example, on the cell into which the polynucleotide is to be introduced, as well as whether the cell is isolated in culture, or is in a tissue or organ in culture or in situ.

A decrease in HYAL2 activity can be detected directly by measuring a decrease in the amount or rate of generation of the pro-inflammatory 20 kDa intermediate HA catabolite following addition of the test agent, or, as discussed above, can be detected indirectly by detecting decreased expression of a reporter gene regulated from a chemokine promoter, which exhibits induced expression in the presence of the 20 kDa intermediate. The term "test agent" is used herein to mean any agent that is being examined for the ability to specifically inhibit HYAL2 activity. As used herein, the term "specifically inhibit", when used in reference to HYAL2 activity, means that the level of HYAL2 activity is reduced by at least about a two-fold greater amount than is the activity of a hyaluronidase that does not have pro-inflammatory. Preferably, an agent that selectively inhibits HYAL2 activity has no effect on the activity of other hyaluronidases such as HYAL1, PH20, or the like.

A test agent can be any type of molecule, including, for example, a peptide, a peptidomimetic, a peptoid such as vinylogous peptoid, a polynucleotide, or a small organic molecule, that one wishes to examine for the ability to specifically inhibit HYAL2 activity. It will be recognized that a method of the invention is readily adaptable to a high throughput format and, therefore, the method is convenient for screening a plurality of test agents either serially or in parallel. A such, a test agent can be one of a plurality of test agents, for example, a library of test agents produced by a combinatorial method. Methods for preparing a combinatorial library of molecules that can be tested for HYAL2 inhibiting activity are well known in the art and include, for example, methods of making a phage display library of peptides, which can be constrained peptides (see, for example, U.S. Pat. No. 5,622,699; U.S. Pat. No. 5,206,347; Scott and Smith, *Science* 249:386–390, 1992; Markland et al., *Gene* 109:13–19, 1991; each of which is incorporated herein by reference); a peptide library (U.S. Pat. No. 5,264,563, which is incorporated herein by reference); a peptidomimetic library (Blondelle et al., *Trends Anal. Chem.* 14:83–92, 1995; a nucleic acid library (O'Connell et al., supra, 1996; Tuerk and Gold, supra, 1990; Gold et al., supra, 1995; each of which is incorporated herein by reference); an oligosaccharide library (York et al., *Carb. Res.*, 285:99–128, 1996; Liang et al., *Science,* 274:1520–1522, 1996; Ding et al., *Adv. Expt. Med. Biol.*, 376:261–269, 1995; each of which is incorporated herein by reference); a lipoprotein library (de Kruif et al., *FEBS Lett.*, 399:232–236, 1996, which is incorporated herein by reference); a glycoprotein or glycolipid library (Karaoglu et al., *J. Cell Biol.*, 130:567–577, 1995, which is incorporated herein by reference); or a chemical library containing, for example, drugs or other pharmaceutical agents (Gordon et al., *J. Med. Chem.*, 37:1385–1401, 1994; Ecker and Crooke, *BioTechnology*, 13:351–360, 1995; each of which is incorporated herein by reference).

Polynucleotides can be particularly useful as agents that can specifically inhibit HYAL2 activity because nucleic acid molecules having binding specificity for cellular targets, including cellular polypeptides, exist naturally, and because synthetic polynucleotides can be readily prepared and those having particular activity can be identified (see, for example, U.S. Pat. No. 5,750,342, which is incorporated herein by reference). The term "polynucleotide" is used broadly herein to mean a sequence of two or more deoxyribonucleotides or ribonucleotides that are linked together by a phosphodiester bond. As such, the term "polynucleotide" includes RNA and DNA, which can be a gene or a portion thereof, a cDNA, a synthetic polydeoxyribonucleic acid sequence, or the like, and can be single stranded or double stranded, as well as a DNA/RNA hybrid. Furthermore, the term "polynucleotide" as used herein includes naturally occurring nucleic acid molecules, which can be isolated from a cell, as well as synthetic molecules, which can be prepared, for example, by methods of chemical synthesis or by enzymatic methods such as by the polymerase chain reaction (PCR). In addition, the polynucleotide can contain nucleoside or nucleotide analogs, or can have a backbone bond other than a phosphodiester bond.

In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. However, a polynucleotide also can contain nucleotide analogs, including non-naturally occurring synthetic nucleotides or modified naturally occurring nucleotides. Such nucleotide analogs are well known in the art and commercially available, as are polynucleotides containing such nucleotide analogs (Lin et al., *Nucl. Acids Res.* 22:5220–5234 (1994); Jellinek et al., *Biochemistry* 34:11363–11372 (1995); Pagratis et al., *Nature Biotechnol.* 15:68–73 (1997), each of which is incorporated herein by reference).

The covalent bond linking the nucleotides of a polynucleotide generally is a phosphodiester bond. However, the covalent bond also can be any of numerous other bonds, including a thiodiester bond, a phosphorothioate bond, a peptide-like bond or any other bond known to those in the art as useful for linking nucleotides to produce synthetic polynucleotides (see, for example, Tam et al., *Nucl. Acids Res.* 22:977–986 (1994); Ecker and Crooke, *BioTechnology* 13:351360 (1995), each of which is incorporated herein by reference). The incorporation of non-naturally occurring nucleotide analogs or bonds linking the nucleotides or analogs can be particularly useful where the polynucleotide is to be exposed to an environment that can contain a nucleolytic activity, including, for example, a tissue culture medium or upon administration to a living subject, since the modified polynucleotides can be less susceptible to degradation.

A polynucleotide comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs into a polynucleotide and, therefore, can be used to produce such a polynucleotide recombinantly from an appropriate template (Jellinek et al., supra, 1995).

As disclosed herein, a polynucleotide HYAL2 specific inhibitor can act by directly binding to and inhibiting HYAL2 activity, or can act by inhibiting HYAL2 gene expression. As such, a polynucleotide HYAL2 specific inhibitor can be an antisense molecule, a ribozyme, a triplexing agent, or an RNA molecule that can mediate RNA interference (RNAi). An antisense polynucleotide, ribozyme or triplexing agent is complementary to a target sequence, which can be a DNA or RNA sequence, for example, a HYAL2 mRNA, and can be a coding sequence, a nucleotide sequence comprising an intron-exon junction, a regulatory sequence such as a Shine-Delgarno sequence, or the like. The degree of complementarity is such that the polynucleotide, for example, an antisense polynucleotide, can interact specifically with the target HYAL2 sequence in a cell. Depending on the total length of the antisense or other polynucleotide, one or a few mismatches with respect to the target sequence can be tolerated without losing the specificity of the polynucleotide for its target sequence. Thus, few if any mismatches would be tolerated in an antisense molecule containing, for example, 20 nucleotides, whereas several mismatches will not affect the hybridization efficiency of an antisense molecule that is complementary, for example, to the full length of a target mRNA encoding a pro-inflammatory hyaluronidase such as HYAL2. The number of mismatches that can be tolerated can be estimated, for example, using well known formulas for determining hybridization kinetics (see Sambrook et al., supra, 1989) or can be determined empirically using methods as disclosed herein or otherwise known in the art, particularly by determining that the presence of the antisense polynucleotide, ribozyme, or triplexing agent in a cell decreases the level of the target sequence or the expression of a polypeptide encoded by the target sequence in the cell.

A polynucleotide useful as an antisense molecule, a ribozyme, a triplexing agent, or RNAi can inhibit translation or cleave the nucleic acid molecule, thereby reducing or inhibiting the amount of HYAL2 in a cell. An antisense molecule, for example, can bind to an mRNA to form a double stranded molecule that cannot be translated in a cell. Antisense oligonucleotides of at least about 15 to 25 nucleotides are preferred since they are easily synthesized and can hybridize specifically with a target sequence, although longer antisense molecules can be expressed from a polynucleotide introduced into the target cell. Specific nucleotide sequences of a HYAL2 gene useful as antisense molecules can be identified using well known methods (see, for example, Seimiya et al., J. Biol. Chem. 272:4631–4636, 1997, which is incorporated herein by reference). Where the antisense molecule is contacted directly with a target cell, it can be operatively associated with a chemically reactive group such as iron-linked EDTA, which cleaves a target RNA at the site of hybridization. A triplexing agent, in comparison, can stall transcription (Maher et al., Antisense Res. Devel. 1:227, 1991; Helene, Anticancer Drug Design 6:569, 1991, each of which is incorporated herein by reference), as can RNAi (Caplen et al., Gene 1–2:95–105, 2000; Oates et al., Devel. Biol. 1:20–28, 2000; Caplen et al., Proc. Natl. Acad. Sci., USA 17:974299747, 2001; Elbashir et al., Nature 6836:494–498, 2001, each of which is incorporated herein by reference).

A HYAL2 specific inhibitor also can be an antibody that specifically bind to HYAL2 and that is identified according to a method of the invention as having the ability to specifically inhibit HYAL2 activity. The term "specifically binds", when used in reference to an antibody, means that an interaction of the antibody and a particular epitope has a dissociation constant of at least about $1 \times 10^{-6}$, generally at least about $1 \times 10^{-7}$, usually at least about $1 \times 10^{-8}$, and particularly at least about $1 \times 10^{-9}$ or $1 \times 10^{-10}$ or less. As such, Fab, $F(ab')_2$, Fd and Fv fragments of an antibody that retain specific binding activity for an epitope of a HYAL2 are included within the definition of an anti-HYAL2 antibody. Preferably, an anti-HYAL2 antibody of the invention specifically binds HYAL2, but does not substantially bind with an epitope of a non-inflammatory hyaluronidase or anti-inflammatory hyaluronidase such as HYAL1, although such crossreactive antibodies may find use as HYAL2 specific inhibitors, provided the crossreactive antibody does not substantially affect the activity of the non-inflammatory or anti-inflammatory hyaluronidase.

The term "antibody" as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains (see Huse et al., Science 246:1275–1281 (1989), which is incorporated herein by reference). These and other methods of making, for example, chimeric, humanized, CDR-grafted, single chain, and bifunctional antibodies are well known to those skilled in the art (Winter and Harris, Immunol. Today 14:243–246, 1993; Ward et al., Nature 341:544–546, 1989; Harlow and Lane, Antibodies: A laboratory manual (Cold Spring Harbor Laboratory Press, 1988); Hilyard et al., Protein Engineering: A practical approach (IRL Press 1992); Borrabeck, Antibody Engineering, 2d ed. (Oxford University Press 1995); each of which is incorporated herein by reference).

Antibodies that bind specifically with a pro-inflammatory hyaluronidase such as HYAL2 can be raised using the hyaluronidase as an immunogen and removing antibodies that crossreact, for example, with HYAL1, PH20, and the like (see Massague, supra, 1998). An antibody of the invention conveniently can be raised using a peptide portion of HYAL2 that is unique to HYAL2, i.e., that is not present in a non-inflammatory or anti-inflammatory hyaluronidase. Where such a peptide is non-immunogenic, it can be made immunogenic by coupling the hapten to a carrier molecule such as bovine serum albumin (BSA) or keyhole limpet hemocyanin (KLH), or by expressing the peptide portion as a fusion protein. Various other carrier molecules and methods for coupling a hapten to a carrier molecule are well known in the art (see, for example, by Harlow and Lane, supra, 1988).

If desired, upon determining that the antibody is a HYAL2 specific inhibitor, a kit incorporating the antibody or other HYAL2 specific inhibitor useful in a method of the invention can be prepared. Such a kit can contain, in addition to the inhibitor, a pharmaceutical composition in which the inhibitor can be reconstituted for administration to a subject. The kit also can contain, for example, reagents for detecting the antibody or other HYAL2 specific inhibitor molecule. Such detectable reagents useful for labeling or otherwise identifying the antibody are described herein and known in the art.

Methods for raising polyclonal antibodies, for example, in a rabbit, goat, mouse or other mammal, are well known in the art (see, for example, Green et al., "Production of Polyclonal Antisera," in *Immunochemical Protocols* (Manson, ed., Humana Press 1992), pages 1–5; Coligan et al., "Production of Polyclonal Antisera in Rabbits, Rats, Mice and Hamsters," in *Curr. Protocols Immunol.* (1992), section 2.4.1; each or which is incorporated herein by reference). In addition, monoclonal antibodies can be obtained using methods that are well known and routine in the art (Harlow and Lane, supra, 1988). For example, spleen cells from a mouse immunized with HYAL2, or an epitopic fragment thereof, can be fused to an appropriate myeloma cell line such as SP/02 myeloma cells to produce hybridoma cells. Cloned hybridoma cell lines can be screened using labeled antigen to identify clones that secrete monoclonal antibodies having the appropriate specificity, and hybridomas expressing antibodies having a desirable specificity and affinity can be isolated and further screened for HYAL2 specific inhibitor activity, such hybridomas providing a continuous source of the antibodies. Such antibodies are useful, for example, for preparing standardized kits for clinical use. A recombinant phage that expresses, for example, a single chain anti-HYAL2 having HYAL2 inhibitor activity also provides an antibody that can used for preparing standardized kits.

Methods of preparing monoclonal antibodies well known (see, for example, Kohler and Milstein, *Nature* 256:495, 1975, which is incorporated herein by reference; see, also, Coligan et al., supra, 1992, see sections 2.5.1–2.6.7; Harlow and Lane, supra, 1988). Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures.

Monoclonal antibodies can be isolated and purified from hybridoma cultures by a variety of well established techniques, including, for example, affinity chromatography with Protein-A SEPHAROSE, size exclusion chromatography, and ion exchange chromatography (Coligan et al., supra, 1992, see sections 2.7.1–2.7.12 and sections 2.9.1–2.9.3; see, also, Barnes et al., "Purification of Immunoglobulin G (IgG)," in *Meth. Molec. Biol.* 10:79–104 (Humana Press 1992), which is incorporated herein by reference). Methods of in vitro and in vivo multiplication of monoclonal antibodies is well known to those skilled in the art. Multiplication in vitro can be carried out in suitable culture media such as Dulbecco's Modified Eagle Medium or RPMI 1640 medium, optionally replenished by a mammalian serum such as fetal calf serum or trace elements and growth sustaining supplements such as normal mouse peritoneal exudate cells, spleen cells, bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo can be carried out by injecting cell clones into mammals histocompatible with the parent cells, for example, syngeneic mice, to cause growth of antibody producing tumors. Optionally, the animals are primed with a hydrocarbon, especially oils such as pristane (tetramethylpentadecane) prior to injection. After one to three weeks, the desired monoclonal antibody is recovered from the body fluid of the animal.

As therapeutic applications for the HYAL2 specific inhibitor antibodies are envisioned, it can be useful to obtain antibodies that have a minimal likelihood of being antigenic in a subject to which the antibody will be administered. As such, where the antibody is to be administered to a human subject, the antibody can be derived from a subhuman primate antibody. General techniques for raising therapeutically useful antibodies in baboons can be found, for example, in Goldenberg et al., International Patent Publication WO 91/11465 (1991); and Losman et al., *Int. J. Cancer* 46:310, 1990, each of which is incorporated herein by reference. A therapeutically useful antibody also can be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are known (see, for example, Orlandi et al., *Proc. Natl. Acad. Sci., USA* 86:3833, 1989, which is hereby incorporated in its entirety by reference). Techniques for producing humanized monoclonal antibodies also are known (see, for example, Jones et al., *Nature* 321:522, 1986; Riechmann et al., *Nature* 332:323, 1988; Verhoeyen et al., *Science* 239:1534, 1988; Carter et al., *Proc. Natl. Acad. Sci., USA* 89:4285, 1992; Sandhu, *Crit. Rev. Biotechnol.* 12:437, 1992; and Singer et al., *J. Immunol.* 150:2844, 1993; each of which is incorporated herein by reference).

HYAL2 specific inhibitor antibodies also can be derived from human antibody fragments isolated from a combinatorial immunoglobulin library (see, for example, Barbas et al., METHODS: *A Companion to Methods in Immunology* 2:119, 1991; Winter et al., *Ann. Rev. Immunol.* 12:433, 1994; each of which is incorporated herein by reference). Cloning and expression vectors that are useful for producing a human immunoglobulin phage library can be obtained, for example, from STRATAGENE Cloning Systems (La Jolla, Calif.). The antibody also can be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described, for example, by Green et al., *Nature Genet.* 7:13, 1994; Lonberg et al., *Nature* 368:856, 1994; and Taylor et al., *Int. Immunol.* 6:579, 1994; each of which is incorporated herein by reference, and are commercially available (Abgenix, Inc.; Fremont Calif.).

Antibody fragments having HYAL2 specific inhibitory activity can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see, for example, Goldenberg, U.S. Pat. No. 4,036,945 and U.S. Pat. No. 4,331,647, each of which is incorporated by reference, and references contained therein; Nisonhoff et al., *Arch. Biochem. Biophys.* 89:230. 1960; Porter, *Biochem. J.* 73:119, 1959; Edelman et al., *Meth. Enzymol.*, 1:422 (Academic Press 1967), each of which is incorporated herein by reference; see, also, Coligan et al., supra, 1992, see sections 2.8.1–2.8.10 and 2.10.1–2.10.4).

Other methods of cleaving antibodies, such as separation of heavy chains to form monovalent light/heavy chain fragments, further cleavage of fragments, or other enzymatic, chemical, or genetic techniques can also be used, provided the fragments specifically bind to the antigen that is recognized by the intact antibody. For example, Fv fragments comprise an association of $V_H$ and $V_L$ chains. This association can be noncovalent (Inbar et al., *Proc. Natl. Acad. Sci., USA* 69:2659, 1972). Alternatively, the variable chains can be linked by an intermolecular disulfide bond or cross-linked by chemicals such as glutaraldehyde (Sandhu, supra, 1992). Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow et al., *Methods: A Companion to Methods in Enzymology* 2:97, 1991; Bird et al., *Science* 242:423–426, 1988; Ladner et al., U.S. Pat. No. 4,946,778; Pack et al., *BioTechnology* 11:1271–1277, 1993; each of which is incorporated herein by reference; see, also Sandhu, supra, 1992. Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick et al., *Methods: A Companion to Methods in Enzymology* 2:106, 1991, which is incorporated herein by reference).

Accordingly, the present invention also relates to a method of ameliorating an inflammatory condition associated with HYAL2 mediated generation of a 20 kDa intermediate HA breakdown product in a subject, by administering a HYAL2 specific inhibitor to the subject. As disclosed herein, the HYAL2 specific inhibitor can be a HYAL2 specific inhibitor identified using a screening assay of the invention, for example, an anti-HYAL2 antibody or a HYAL2 binding fragment of said antibody, which specifically binds to and inhibits the activity of HYAL2 without affecting non-inflammatory or anti-inflammatory hyaluronidases, a polynucleotide, peptide, small organic molecule, or the like having HYAL2 specific inhibitory activity; or can be a polynucleotide that modulates HYAL2 gene expression, for example, an antisense molecule, a ribozyme, a triplexing agent, or an RNA molecule that mediates RNAi.

For example, the methods of the invention are useful for treating a subject suffering from, or predisposed to, a vasculitis associated with HYAL2 activity. Vasculitis disorders are well known. For example, the signs and symptoms of Wegener's granulomatosis have been shown to correlate with insufficient HYAL1 activity. Wegener's granulomatosis is a systemic necrotizing vasculitis that involves small arteries and veins, and is characterized by granulomatous lesions of the respiratory tract, including the lung; kidney, particularly renal glomerular tissue; and spleen (Rubin and Farber, supra, 1999; pages 517–518). It is more common in men than women, and presents in the fifth or sixth decades of life. Lung involvement occurs in greater than 90% of patients, with a persistent bilateral pneumonitis being most prominent. Radiologic analysis reveals multiple pulmonary infiltrates. Eighty percent of untreated patients die within one year, though treatment with cyclophosphamide can result in significant improvement, including remission and long term disease free periods (Id.). Although circulating ANCA are found in 90% of cases, the etiology of Wegener's granulomatosis has not previously been described.

As disclosed herein, a vasculitis amenable to treatment according to a method of the invention is characterized by an elevated level in the blood of an approximately 20 kDa intermediate breakdown product of HA due to HYAL2 activity. As used herein, the term "elevated", when used in reference to the level of the 20 kDa intermediate in the blood of a subject, means that the amount of the intermediate in the subject's blood is greater than the amount at which the 20 kDa intermediate generally is found in a healthy age and gender matched individual (also referred to herein as a "normal" level). The term "normal" is used herein to refer to a mean value, which can include a range of values comprising the mean bounded by one or more standard deviations, that is generally found in a healthy population of individuals, which can be a random population or specifically biased population. A normal value for a biological material such HA or HYAL2 in a particular biological sample such as blood plasma or serum sample can be determined using routine statistical sampling methods. For example, a population of healthy individuals can be tested for the level or activity of the particular biological material such as HA or HYAL2, and the mean and standard deviation of measured levels or activities can be determined. If desired, the population of individuals examined can be a randomly selected population, or can be a biased population, in which individuals within a specified age range; or all males or all females, or a combination of males and females; or the like, are selected.

The method used to determine the level of the 20 kDa HA intermediate can be any method as disclosed herein or otherwise known in the art. For example, HA levels can be detected using a radioassay based on the binding of HA to an HA binding protein isolated from bovine cartilage (see, for example, Tengblad, *Biochim. Biophlys. Acta* 578:281, 1979; Engstrom-Laurent et al., *Scand. J. Clin. Lab. Invest.* 45:497–504, 1985; Laurent and Tengblad, *Anal. Biochem.* 109:386–394, 1980, each of which is incorporated herein by reference). In addition, HA levels can be determined using a kit from a commercially available source such as Corgenix, Inc., Chugai, or Pharmacia. In addition, a method such as that described by West and Yaqoob (supra, 1997), who determined, in a population of 31 individuals, that serum HA was present at about 90.26+/−37.18 μg/ml, can be used to determine total circulating HA, and can further include a method such as gel electrophoresis to determine the percent of the total HA measured that is attributable to the 20 kDa intermediate. The level of activity of HYAL1 and HYAL2 in a sample can be determined using a method as disclosed herein (see Examples 1 and 2) or otherwise known in the art, for example, a zymography method (Podyma et al., Biochem. Biophzys. Res. Comm. 241:446–452, 1997, which is incorporated herein by reference).

Although reference is made herein generally to a blood level or circulating level of the 20 kDa intermediate HA catabolite, an assay to determine such as level or activity typically is performed using plasma fraction or serum fraction of whole blood. Similarly, however, a level of the 20 kDa HA intermediate or a level or activity of HYAL2 can be determined in other biological samples, including, for another biological fluid such as synovial fluid, urine, or sputum; or a tissue or organ sample such as a lung, liver, or kidney biopsy sample, or any other such sample in which HYAL2 generally is expressed.

A method of the invention provides a means to ameliorate an inflammatory disorder associated with increased HYAL2 activity, or with decreased activity of a hyaluronidase such as HYAL1, which breaks down the pro-inflammatory 20 kDa intermediate to non-inflammatory oligosaccharides. As used herein, the term "ameliorate" means that signs or symptoms associated with the inflammatory disorder are lessened. The signs or symptoms to be monitored will be characteristic of the particular inflammatory disorder and will be well known to skilled clinician, as will the methods for monitoring the signs and conditions. For example, methods of determining that treatment of a Wegener's granulomatosis is responding to treatment with cyclophosphamide similarly can be used to determine that a method of the invention is ameliorating the vasculitis in the subject. Since a method of the invention is designed to decrease the levels of the 20 kDa HA intermediate in the circulation, or in a compartment of the eye, it will be recognized that a determination that a method of the invention is ameliorating the inflammatory disorder also can be made by detecting a decrease in the level of the 20 kDa HA intermediate breakdown product, for example, in the plasma.

A vasculitis amenable to treatment according to a method of the invention can be any vasculitis associated with increased HYAL2 activity, which allows an accumulation of a greater than normal level of the pro-inflammatory 20 kDa HA intermediate breakdown product. As such, the inflammatory disorder can be a vasculitis such as Wegener's granulomatosis; a vasculitis of the polyarteritis nodosa group of systemic necrotizing vasculitis such as polyarteritis nodosa or allergic angiitis and granulomatosis (Churg-Strauss variant); a hypersensitivity vasculitis such as serum sickness, Henoch-Schönlein purpura, vasculitis associated with a connective tissue disorder, or vasculitis associated with essential mixed cryogloulinemia; a giant cell arteritis such as temporal arteritis or Takayasu arteritis; Kawasaki disease; thromboangiitis obliterans; or Behcet disease.

Generally, a vasculitis amenable to treatment according to a method of the invention is a small vessel vasculitis or a medium vessel vasculitis. Small vessel vasculitis disorders can present clinical signs and symptoms in or more of various tissues and organs, including, for example, a palpable purpura (skin, "vasculitic rash"); glomerulonephritis (kidney); meningeal inflammation (central nervous system, "CNS"); polyneuropathy (peripheral nervous system, "PNS"); pericarditis (heart); pain or gastrointestinal hemorrhage (gastrointestinal tract, "GI"); arthralgia or arthritis (joints); and/or myalgia (muscle). Similarly, a medium vessel vasculitis can present clinical signs and symptoms, including, for example, nodules, ulcers or gangrene (skin); glomerulonephritis or hypertension (kidney); a focal cranioneuropathy or other focal CNS sign or symptom (CNS); mononeuritis multiplex (PNS); infarction (heart); pain, GIB, or perforation (GI); arthralgia or arthritis (joint); and/or tenderness (muscle). A vasculitis amenable to treatment according to a method of the invention. A large vessel vasculitis can present clinical signs and symptoms such as atherosclerosis (blood vessels of the skin), HTN or infarction (kidney), focal CNS (CNS), infarction or bruits (heart), ischemic bowel (GI), arthralgia or arthritis (joint), and/or claudication (muscle).

In the eye, insufficient HA catabolism can result in severe pathologic conditions and ocular complications due to increased intraocular pressure. Ocular abnormalities, in addition to vascular and inflammatory abnormalities, have been observed in HYAL1 knockout mice, in which accumulation of the 20 kDa intermediate occurs. Blindness frequently occurs in older male knockout mice (greater than 5 months of age) that do not die of pulmonary or ulcerative complications. Swelling of the eye accompanies opacity of the lens and loss of corneal transparency. Various forms of vasculitis such as giant cell arteritis, temporal vasculitis, and polyarteritis nodosa frequently result in blindness occurring as a result of ocular inflammation. Localized ocular accumulation of intermediate HA breakdown products, including the 20 kDa intermediate, can be a primary factor responsible for the increased intraocular pressure associated with ophthalmic disorders that occur in association with glaucoma or Graves' disease.

A pathologic condition associated with increased HYAL2 activity can be identified by detecting increased HYAL2 activity in a biological sample of the subject. Upon determining that a subject has a pathologic conditions such as a cancer or an inflammatory disorder associated with increased HYAL2 activity, or upon determining that the subject has a level of HYAL 1 activity or other anti-inflammatory hyaluronidase that is decreasing over a period of time, thus rendering the subject susceptible to and, therefore, predisposed to developing the pathologic condition, the condition can be ameliorated by specifically inhibiting the HYAL2 activity in the subject by administering a HYAL2 specific inhibitor to the subject.

For administration to a living subject, including a human or other subject, the HYAL2 specific inhibitor generally is formulated with a pharmaceutically acceptable carrier to provide a composition suitable for administration the subject. The form of the composition will depend, in part, on the route by which the composition is to be administered. Generally, the composition will be formulated such that the HYAL2 inhibitor is in a solution or a suspension, such a form be suitable for administration by injection, infusion, or the like, or for aerosolization for administration by inhalation. However, the composition also can be formulated as a cream, foam, jelly, lotion, ointment, gel, or the like. Alternatively the molecule may be formulated in an orally available A pharmaceutically acceptable carrier useful for formulating a composition for use in a method of the invention can be aqueous or non-aqueous, for example alcoholic or oleaginous, or a mixture thereof, and can contain a surfactant, emollient, lubricant, stabilizer, dye, perfume, preservative, acid or base for adjustment of pH, a solvent, emulsifier, gelling agent, moisturizer, stabilizer, wetting agent, time release agent, humectant, or other component commonly included in a particular form of pharmaceutical composition. Pharmaceutically acceptable carriers are well known in the art and include, for example, aqueous solutions such as water or physiologically buffered saline or other solvents or vehicles such as glycols, glycerol, oils such as olive oil or injectable organic esters. A pharmaceutically acceptable carrier can contain physiologically acceptable compounds that act, for example, to stabilize or to increase the absorption of the HYAL2 specific inhibitor, for example, carbohydrates, such as glucose, sucrose or dextrans, antioxidants, such as ascorbic acid or glutathione, chelating agents, low molecular weight proteins or other stabilizers or excipients.

The pharmaceutical composition also can comprise an admixture with an organic or inorganic carrier or excipient, and can be compounded, for example, with the usual non-toxic, pharmaceutically acceptable carriers for tablets, pellets, capsules, suppositories, solutions, emulsions, suspensions, or other form suitable for use. The carriers, in addition to those disclosed above, can include glucose, lactose, mannose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition, auxiliary stabilizing, thickening or coloring agents can be used, for example a stabilizing dry agent such as triulose.

Where a polynucleotide HYAL2 specific inhibitor is used, it can be incorporated within an encapsulating material such as into an oil-in-water emulsion, a microemulsion, micelle, mixed micelle, liposome, microsphere or other polymer matrix (see, for example, Gregoriadis, *Liposome Technology*, Vol. 1 (CRC Press, Boca Raton Fla. 1984); Fraley et al., *Trends Biochem. Sci.*, 6:77, 1981). Liposomes, for example, which consist of phospholipids or other lipids, are nontoxic, physiologically acceptable and metabolizable carriers that are relatively simple to make and administer. "Stealth" liposomes (see U.S. Pat. Nos. 5,882,679; 5,395,619; and 5,225,212) are an example of such encapsulating materials particularly useful for preparing a pharmaceutical composition.

The amount HYAL2 specific inhibitor contained in a composition can be varied, depending on the type of composition, such that the amount present is sufficient to reduce the level of the 20 kDa HA intermediate in the circulation or in a target tissue. In general, an amount of a composition sufficient to reduce the level of the 20 kDa HA intermediate will be determined using routine clinical methods, including Phase I, II and III clinical trials.

The following examples are intended to illustrate but not limit the invention.

EXAMPLE 1

HYALURONIDASE ASSAYS

Hyaluronan concentration and hyaluronidase activity can be assayed by using different techniques including turbidimetry, viscometry, ELISA, chromatography, and colorimetry. A convenient colorimetric method is that of Reissig et al. (*J. Biol. Chem.* 217:959–966, 1955), in which the color results from a reaction between the Ehrlich's reagent (DMAB) and the N-acetyl-d-glucosamine reducing end of each hyaluronan chain. The turbidity at 585 nm, the wavelength at which the color intensity is maximal, may be estimated by curve fitting the spectrum between 450 nm and 650 nm. Subtracting the turbidity from the absorbance gives the calorimetric intensity which represents the concentration of polysaccharide chains. Moreover, the turbidity may give additional information about the existence of polysaccharide-protein complexes and their nature.

This example provides methods for the turbidometric determination of HYAL2 and HYAL1 activities.

METHODS

Hyaluronic acid (hyaluronan; HA) is measured in a homogeneous assay by its ability to form turbidity with an acid albumin solution. Turbidity is a function of HA concentration and can be related to enzyme activity. One unit corresponds to a USP/National Formulary Unit and is referenced to a standard USP/NF hyaluronidase.

REAGENTS 0.1 M sodium phosphate buffer, pH 5.3, with 0.15 M sodium chloride (HSE buffer); 0.5 M sodium acetate buffer, pH 4.2.

Albumin reagent is prepared by dissolving 2.5 grams of bovine serum albumin, Fraction V, in 250 ml of 0.5 M sodium acetate buffer, pH 4.2, adjusting the pH to 3.0 with 2 N HCl, heating to 93° C. for 30 min, cooling, and adjusting the final volume to 1000 ml with 0.5 ml sodium acetate buffer, pH 4.2.

USP/NF Standard: Prepare stock solutions of 1.0 and 0.5 mg/ml.

A stock HA preparation is prepared as follows: Dissolve 10 mg Worthington hyaluronic acid (Code: VHHA) in 25 ml 0.1 M sodium phosphate buffer (pH 5.3) with 0.15 M sodium chloride. This solution can be prepared by allowing VHHA to dissolve overnight. Heating in a boiling water bath for 10–15 min can be used if the material is not immediately soluble.

For enzyme, prepare a stock solution at 1 mg/ml in 0.1 M sodium phosphate buffer (pH 5.3) with 0.15 M sodium chloride. Immediately prior to use dilute further in the same buffer. For crude grade material concentrations of 0.01–0.05 mg/ml are recommended. For purified grade concentration of 0.001–0.01 mg/ml are recommended.

PROCEDURE

Preparation of "Standard Curve". Into a series of numbered tubes, pipette as follows:

|         | Corresponding to | | |
| --- | --- | --- | --- |
| Tube #1 | ml HA | mg HA | ml HSE buffer |
| 1 | 0.00 | 0.00 | 1.00 |
| 2 | 0.10 | 0.04 | 0.90 |
| 3 | 0.20 | 0.08 | 0.80 |
| 4 | 0.25 | 0.10 | 0.75 |
| 5 | 0.30 | 0.12 | 0.70 |
| 6 | 0.40 | 0.16 | 0.60 |
| 7 | 0.50 | 0.20 | 0.50 |
| 8 | 0.60 | 0.24 | 0.40 |
| 9 | 0.70 | 0.28 | 0.30 |
| 10 | 0.80 | 0.32 | 0.20 |

Place all tubes in a boiling water bath for 5 min. Cool to room temperature. Add 9.0 ml of albumin reagent and allow to stand for 10 min. Read absorbance at 540 nm. Plot absorbance at 540 nm versus mg HA to form standard curve. HA should be soluble under the defined conditions and should produce a standard curve with a slope of 1.5 or greater.

For the "Test Procedure", pipette 0.5 ml of a 0.4 mg/ml HA solution into a series of test tubes. Incubate at 37° C. for 4–5 min to achieve temperature equilibrium. Incubate one blank tube with 1 ml of 0.1 M sodium phosphate buffer, pH 5.3, with 0.15 M sodium chloride. At timed intervals add 0.5 ml of appropriately diluted enzyme or NF standard to respective tubes. Incubate each tube exactly 10 min and cool in an ice bath to room temperature. Add 9.0 ml of albumin reagent to each tube and incubate at room temperature for 10 min. Read Absorbance at 540 nm (A540) of each tube against the blank.

The amount of hyaluronic acid remaining after digestion is determined from the standard curve.

Calculate the amount of hyaluronic acid digested as follows: mg HA digested=0.2 mg−mg HA remaining Calculate turbidity reducing units/mg of enzyme or standard as follows: TRU/mg−(mg HA digested×3.0)/(mg enzyme in reaction)

Calculate USP/NF units ("U")/mg enzyme as follows: (USP/NF U/mg stnd)/(TRU/mg stnd)=(USP/NF U/mg sample)/(TRU/mg sample)

EXAMPLE 2

MICROTITER-BASED ASSAY FOR HYAL1 ACTIVITY

The following example provides a sensitive, rapid microtiter-based assay for determining HYAL1 activity.

The free carboxyl groups of HA are biotinylated in a one step reaction using biotin-hydrazide. This substrate is covalently coupled to a 96 well microtiter plate. At the completion of the enzyme reaction, residual substrate is detected with an avidin-peroxidase reaction that can be read in a standard ELISA plate reader. As the substrate is covalently bound to the microtiter plate, artifacts such as pH-dependent displacement of the biotinylated substrate does not occur. The sensitivity permits rapid measurement of hyaluronidase activity from cultured cells and biological samples with an inter-assay variation of less than 5%.

The hyaluronidase assay is exemplified by determining the distribution profile of plasma hyaluronidase levels in normal human sera. A 1 µl sample of plasma was sufficient for assays in triplicate. Hyaluronidase activity in human foreskin primary keratinocyte cultures was also quantitated. A twenty-five fold increase in hyaluronidase activity was observed in keratinocyte cultures induced to differentiate in high calcium (1.5 mM), compared to levels in low calcium (0.05 mM) media. The microtiter-based assay can be used conveniently as a routine clinical laboratory procedure.

Hyaluronidases are a family of β 1–4 endoglucosaminidases that degrade HA and, from vertebrate sources, to a lesser extent, glycosaminoglycans. Commonly used hyaluronidase assays have been based upon the measurement of the generation of new reducing N-acetylamino groups (Bonner and Cantey, *Clin. Chim. Acta* 13:746–752, 1966, which is incorporated herein by reference), or loss of viscosity (De Salegui et al., *Arch. Biochem. Biophys.* 121:548–554, 1967, which is incorporated herein by reference) or turbidity (Dorfman and Ott, *J. Biol. Chem.* 172:367, 1948, which is incorporated herein by reference). More recently, a new generation of assays have been developed. A previously described microtiter-based assay requires the preparation of a highly specialized reagent, a hyaluronan-binding peptide derived from the proteoglycan, aggrecan (Stern and Stern, *Matrix* 12:397–403, 1992, which is incorporated herein by reference). The peptide is obtained from tryptic digests of bovine nasal cartilage and isolated by HA-affinity chromatography, then is biotinylated (Id.). Residual substrate in the microtiter plate is determined as a measure of enzymatic activity.

Hyaluronidases from vertebrate tissues can be separated into two classes—those such as PH20, which has a maximal activity near neutral pH, and the lysosomal (acid-active) enzymes with maximal activity below pH 4.0. The present assay was used to track enzyme activity in the purification and expression of HYAL1 from human plasma. The assay is as sensitive as previously described assays, can be performed using an incubation of about 15 to 60 min, and does not require preliminary preparation of a complex bioreagent.

METHODS

One hundred mg of human umbilical cord HA (ICN Pharmaceuticals; Irvine Calif.) was dissolved in 0.1 M MES, pH 5.0, to a final concentration of 1 mg/ml and allowed to dissolve for at least 24 hr at 4° C. prior to coupling of biotin. Sulfo-NHS (Pierce; Rockford Ill.) was added to the hyaluronate MES solution to a final concentration of 0.184 mg/ml. Biotin hydrazide (Pierce) was dissolved in DMSO as a stock solution of 100 mM and added to the HA solution to a final concentration of 1 mM. A stock solution of 1-ethyl-3-(3-dimethylaminopropyl) carbodiimide (EDAC) was prepared as a 100 mM stock solution in distilled water and added to the HA biotin solution at a final concentration of 30 mM. This solution was left stirring overnight at 4° C. Unlinked biotin and EDAC were removed by dialysis against water with 3 changes of 1000× volume of water. The dialyzed, biotinylated HA (bHA) was aliquoted and stored at −20° C. for up to several months.

Sulfo-NHS was diluted to 0.184 mg/ml in water with the bHA at a concentration of 0.2 mg/ml and pipetted into 96 well COVALINK-NH plates (NUNC; Placerville N.J.) at 50 µl per well. EDAC was diluted to 0.123 mg/ml in water and pipetted into the COVALINK-NH plates with the HA solution resulting in a final concentration of 10 µg/well hyaluronate and 6.15 µg/well EDAC. The plates were incubated overnight at 4° C. or for 2 hr at 23° C., which gave comparable results. After covalent immobilization of bHA on the microtiter plates, the coupling solution was removed by shaking and the plates were washed 3 times in PBS containing 2M NaCl and 50 mM MgSO4 (Buffer A). The plates could be stored at 4° C. for up to one week.

The COVALINK-NH plates with immobilized bHA were equilibrated with 100 µl/well assay buffer—either 0.1 M forinate, pH 3.7, 0.1 M NaCl, 1% TRITON X-100 detergent, 5 mM saccharolactone for lysosomal hyaluronidase; or 0.1 M formate pH 4.5, 0.15 M NaCl, 1% TRITON X-100 detergent, 5 mM saccharolactone for neutral-active enzymes. A set of standards for the calibration of enzyme activity against "relative Turbidity Reducing Units" (rTRU's) was generated by diluting WYDASE® hyaluronidase (Wyeth-Ayerst) in neutral enzyme buffer from 1.0 to $1\times10^{-6}$ rTRU/well and assaying 100 µl/well in triplicate. Samples of acid-active hyaluronidase were diluted in lysosomal assay buffer from 1:10 to 1:130,000 in immunoaffinity-purified preparations of recombinant human plasma hyaluronidase (Frost et al., supra, 1997) and were pipetted in triplicate at 100 µl/well. For most assays of tissue extracts and human plasma, a 30 min incubation at 37° C. was sufficient. Positive and negative control wells (no enzyme or no ABC (see below), respectively) were included in triplicate.

The reaction was terminated by the addition of 200 µl/well of 6M Guanidine HCl followed by three washes of 300 µl/well with PBS, 2 M NaCl, 50 mM $MgSO_4$, 0.05% TWEEN 20 detergent (Buffer B). An avidin biotin complex (ABC) kit (Vector Labs; Burlingame Calif.) was prepared in 10 ml of PBS containing 0.1% TWEEN 20 detergent, which was preincubated for 30 min at room temperature during the hyaluronidase incubation. The ABC solution was added (100 μl/well) and incubated for 30 min at room temperature. The plate was washed five times with Buffer B, then an o-phenylenediamine (OPD) substrate was added at 100 μl/well by dissolving one 10 mg tablet of OPD in 10 ml of 0.1 M citrate-$PO_4$ buffer, pH 5.3 and adding 7.5 μl of 30% $H_2O_2$. The plate was incubated in the dark for 10–15 min, then read using a 492 nm filter in an ELISA plate reader (Titertek Multiskan PLUS; ICN) monitored by computer using the Delta Soft II plate reader software from Biometallics (Princeton N.J.). A standard curve using the bovine testicular hyaluronidase was generated by a four parameter curve fit of the commercial hyaluronidase preparation and unknown samples were interpolated through their absorbance at 492 nm.

Three different hyaluronidases were used for the analysis of time dependence of HA degradation. Using 0.01 rTRU of immunoaffinity purified recombinant human plasma hyaluronidase (600,000 rTRU/mg), bovine testicular hyaluronidase (Sigma Type VI-s 3,000 TRU/mg), or *Streptomyces* hyaluronidase (Calbiochem) samples were placed into a microtiter bHA plate at 0, 5, 10, 15 and 30 min in a 37° C. water bath. Samples were then processed and bHA degradation measured at 492 nm.

To analyze pH dependence of hyaluronidases, immunoaffinity purified recombinant human plasma hyaluronidase and bovine testicular hyaluronidase were used. The pH dependence of enzyme activity was measured by diluting purified plasma hyaluronidase or partially purified bovine testicular hyaluronidase to 0.1 rTRU in the following buffers: 50 mM formate, pH 3–4.5; 50 mM acetate, pH 5–6; 50 mM MES, pH 6–7; or 50 mM HEPES, pH 7–8. Samples were assayed for 30 min at 37° C. and activity was expressed as a percent of maximal activity. NaCl was not used in buffers, as it can alter the pH optima of testicular hyaluronidase preparations (Gold, *Biochem. J.* 205:69–74, 1982; Gacesa et al. *Biochem. Soc. Trans.* 7:1287–1289, 1979); physiological salt concentrations (0.15 M) decreased the apparent pH optimum, an effect that was more pronounced in purified preparations of the testicular enzyme than in the original crude sample.

Levels of hyaluronidase in human plasma were established from 40 normal human plasma samples, all of which were collected in EDTA. Residual cellular material was removed by centrifugation. Plasma samples were assayed after a 30 min incubation using 1:200 dilutions in the formate assay buffer.

Hyaluronidase activity also was characterized in normal keratinocytes. Primary foreskin keratinocyte cultures were generated from circumcision tissue from newborn animals. Briefly, tissue was washed 5× in PBS with penicillin, streptomycin, and fungizone, followed by digestion overnight at 4° C. in dispase. Epithelium was stripped from mesenchymal tissue with forceps and digested in trypsin followed by plating on collagen-coated plates in KGM (keratinocyte growth medium) with 0.05 mM calcium (Clonetics; San Diego Calif.). Cells were used between the first and fourth passage. To test the effects of induction of differentiation on hyaluronidase activity, cells were plated into 6 well plates and, at confluence, the medium was either replaced with fresh KGM with 0.05 mM calcium or changed to KGM with 1.5 mM calcium.

Cell layers and conditioned media were harvested after 72 hr in culture. Cell layers were harvested with 60 mM octylglucoside with 50 U/ml DNase I (Boehringer Mannheim; Indianapolis Ind.) and Complete™ protease inhibitor cocktail (Boehringer Mannheim) in PBS. Cells were extracted for 30 min on ice followed by centrifugation at 10,000× g for 10 min. Conditioned media from each sample was treated with octylglucoside and protease inhibitors. Cell extracts were normalized on the basis of total cellular protein using the BioRad Protein Assay kit (BioRad, Richmond Calif.). Extracts were assayed at 1:10 dilutions in formate assay buffer at 37° C. for 60 min. Activity was expressed as rTRU/mg cellular protein.

RESULTS

HA from human umbilical cord was biotinylated in a one step reaction using biotin-hydrazide and EDAC. By limiting the EDAC, which couples the free carboxyl groups on HA with biotin hydrazide, only a small fraction of the total glucuronic acid residues on HA were labeled. This amount of EDAC ($3\times10^{-5}$ M) added to HA ($2.8\times10^{-3}$ M) results in a maximum of one molecule of biotin hydrazide coupled per 93 disaccharide units of HA.

The bHA reagent was used to generate a microtiter-based hyaluronidase assay. The bHA was coupled to NH-bearing microtiter plates at a final concentration of 10 μg/well using EDAC. The amount of HA bound to the plates through this procedure was assayed with the HABP hyaluronan assay (Seigukagu, Japan; or HA-50 kit, Pharmacia). Based upon the HABP hyaluronan assay, approximately 7.5 μg of the 10 μg added per well bound to the plate.

A four parameter curve fit of bovine testicular hyaluronidase standard reactions measured at pH 3.7, and diluted from 1.0 to $1\times10^{-6}$ TRU/well, was prepared. Four parameter curve fits were established from the equation $y=((A-D)/(1+(conc/C)^B))+D$ where logit $y=1n\ (y'/1-y')$, $y'=(y-D)/(A-D)$, $B=-b/1n\ 10$ and $C=EXP(a/B)$. The four parameters (A,B,C,D) were calculated with a software program that utilized the 2+2 algorithm with linear regression (Rodbard et al., *Clin. Chem.* 22:350, 1976). This curve fit incorporates the sigmoidal aspects the standard curve. Optimal accuracy for measurement of a sample occurred from 0.001 to 0.01 TRU/well. During a 30 min incubation, 1/1000th of a TRU is clearly detectable. A standard logarithmic curve also can be utilized over a shorter range of values to establish a standard curve fit.

To establish linearity of the assay over time, samples of plasma, *Streptomyces*, and testicular hyaluronidase were assayed as a function of time. Linearity was observed over a 30 min incubation of enzyme for recombinant human plasma hyaluronidase, whereas preparations of testicular hyaluronidase and *Streptomyces* hyaluronidase slightly deviated from linearity. Log dilutions of human plasma hyaluronidase revealed that linearity was observed in more dilute preparations, presumably where substrate had not become limiting.

The pH dependence of a neutral-active and an acid-active hyaluronidase were examined. Recombinant human plasma hyaluronidase was compared to a commercial preparation of bovine testicular hyaluronidase (Sigma, Type VI-S). The plasma enzyme had an acid optimum at pH 3.8, with no detectable activity above pH 4.5, whereas the bovine testicular hyaluronidase had a bimodal distribution of activity with optima at pH 4.5 and pH 7.5.

Hyaluronidase activity from the plasma of normal donors was assayed to establish the distribution of hyaluronidase levels in the human circulation. The distribution of hyaluronidase activity assayed at pH 3.7 from 40 healthy male and female subjects from 20 to 70 years of age revealed a mean plasma hyaluronidase level of 5.9 rTRU/ml with a standard deviation of 1.2 rTRU. The inter-assay and intra-assay variations established from repeated sampling of a single plasma sample were less than 5% and 10%, respectively, thus establishing the reproducibility of this procedure. The inter-assay variation was calculated from comparing the standard deviation of the interpolated values of a serum sample assayed in 10 different wells in a single plate to the mean interpolated value of those ten wells against a standard curve. The intra-assay variation was obtained from comparing the standard deviation of interpolated values from the serum sample assayed in six different plates with different standard curves to the mean interpolated value of those six samples.

Primary cultures of keratinocytes can be induced to stratify and express several markers for differentiation in a defined culture medium when calcium levels are elevated from 0.05 mM to 1.5 mM (Hennings and Holbrook, *Expt. Cell Res.* 143:127–142, 1983). The effect of calcium-induced differentiation (1.5 mM calcium) in keratinocyte cultures resulted in an approximately 25-fold increase in hyaluronidase activity in both conditioned media and cell layer, as compared to cultures in 0.05 mM calcium. EDTA was included with protease inhibitors in the extraction buffer, making it unlikely that calcium was directly effecting enzymatic activity. In purified preparations of human plasma hyaluronidase, EDTA had no inhibitory effect on enzyme activity, nor did added calcium have a stimulatory effect. All of the hyaluronidase activity secreted into the media of the keratinocyte cultures was immunoprecipitated with monoclonal antibodies against the plasma enzyme.

These results demonstrate that the hyaluronidase assay is very sensitive over short incubation periods, and is approximately 1,000 times more sensitive than other commonly used assays performed under identical incubation times. Increased sensitivity for detecting enzyme in cell cultures that produce very low levels of activity can be obtained by using a longer incubation time of 2 to 12 hr. The use of a four parameter cure fit has a semi-logarithmic relationship over a three log range between absorbance and activity, from 0.6 to 0.006 TRU/ml during a 30 min incubation. If the incubation is extended to 2 hr, the curve shifts from 0.06 to 0.00006 TRU/ml, resulting in a more sensitive measurement of activity. Routinely, a one hour incubation is used for cell culture extracts and the 30 min assay for tissue extracts. In addition, the assay is useful for measuring the pH optima of various enzymes. For example, immunoaffinity purified plasma hyaluronidase showed a characteristic acid pH optimum of 3.8, whereas the commercial semi-purified preparation of bovine testicular hyaluronidase contained two distinct peaks of activity, one at neutrality and one at pH 4.0. The pH profile of immunoaffinity-purified recombinant human plasma hyaluronidase was identical to that of unprocessed human plasma; no activity was detected at neutral pH.

Although the invention has been described with reference to the above examples, it will be understood that modifications and variations are encompassed within the spirit and scope of the invention. Accordingly, the invention is limited only by the following claims.

What is claimed is:

1. A method of identifying an agent that specifically inhibits hyaluronidase 2 (HYAL2) activity, the method comprising:
contacting HYAL2 and high molecular weight substrate with a test agent, under conditions suitable for HYAL2 activity; and
detecting a decrease in HYAL2 activity due to contact with the test agent, wherein the test agent does not substantially affect activity of an anti-inflammatory hyaluronidase, thereby identifying an agent that specifically inhibits HYAL2 activity.

2. The method of claim 1, wherein the HYAL2 comprises a detergent extract of a cell.

3. The method of claim 1, wherein the HYAL2 comprises an intact cell, which expresses HYAL2 on the plasma membrane surface.

4. The method of claim 3, wherein the HYAL2 is endogenous to the cell.

5. The method of claim 3, wherein the HYAL2 is expressed from a transgene.

6. The method of claim 1, wherein the HYAL2 is reconstituted in a synthetic membrane.

7. The method of claim 6, wherein the synthetic membrane comprises a liposome.

8. The method of claim 1, wherein the anti-inflammatory hyaluronidase is hyaluronidase 1.

9. The method of claim 1, wherein detecting a decrease in HYAL2 activity comprises detecting decreased generation of a 20 kDa intermediate HA catabolite in the presence of the test agent as compared to the absence of the test agent.

10. The method of claim 1, wherein detecting a decrease in HYAL2 activity comprises detecting a change in expression of a reporter gene in the presence of the test agent as compared to the absence of the test agent.

11. The method of claim 10, wherein the reporter gene is luminescent polypeptide, chemiluminescent polypeptide, fluorescent polypeptide, or an enzyme.

12. The method of claim 11, wherein the enzyme is β-lactamase, chloramphenicol acetyltransferase, adenosine deaminase, aminoglycoside phosphotransferase, dihydrofolate reductase, hygromycin-B phosphotransferase, thymidine kinase, β-galactosidase, luciferase, or xanthine guanine phosphoribosyltransferase polypeptide.

13. The method of claim 12, wherein the fluorescent polypeptide is a green fluorescent protein.

14. The method of claim 10, wherein the reporter gene comprises a chemokine promoter.

15. The method of claim 14, wherein the chemokine promoter is a RANTES promoter, an MIP1 promoter, an MIP2 promoter, an interleukin promoter, a metalloproteinase promoter, or an inducible nitric oxide synthase promoter.

16. The method of claim 1, wherein the agent is a peptide, a polynucleotide, a peptidomimetic, a peptoid, or a small organic molecule.

17. The method of claim 1, wherein the agent is an anti-HYAL2 antibody, or a HYAL2 binding fragment of said antibody.

18. The method of claim 17, wherein the HYAL2 binding fragment of said antibody is an Fab fragment, an F(ab')$_2$ fragment, an Fd fragment, or an Fv fragment.

19. A hyaluronidase 2 (HYAL2) specific inhibitor obtained by the method of claim 1.

20. A composition, comprising the HYAL specific inhibitor of claim 19.

21. The composition of claim 20, which is suitable for administration to a subject.

22. The composition of claim 21, wherein the subject is a mammal.

23. A method of ameliorating an inflammatory condition associated with hyaluronidase 2 (HYAL2) mediated generation of a 20 kDa intermediate hyaluronan breakdown product in a subject, the method comprising administering a HYAL2 specific inhibitor to the subject, whereby HYAL2 activity is reduced or inhibited, thereby ameliorating the inflammatory condition in the subject.

24. The method of claim 23, wherein the HYAL2 specific inhibitor is the HYAL2 specific inhibitor of claim 19.

25. The method of claim 23, wherein the HYAL2 specific inhibitor is an anti-HYAL2 antibody or a HYAL2 binding fragment of said antibody.

26. The method of claim 23, wherein the HYAL2 specific inhibitor is a polynucleotide.

27. The method of claim 26, wherein the polynucleotide modulates HYAL2 gene expression.

28. The method of claim 27, wherein the polynucleotide is an antisense molecule, a ribozyme, a triplexing agent, or an RNA molecule that mediates RNA interference.

* * * * *

SEQUENCE LISTING

<160> NUMBER OF SEQ ID NOS: 2

<210> SEQ ID NO 1
<211> LENGTH: 1450
<212> TYPE: DNA
<213> ORGANISM: Homo sapiens
<220> FEATURE:
<221> NAME/KEY: misc_feature
<222> LOCATION: (1438)..(1438)
<223> OTHER INFORMATION: n is any nucleotide

<400> SEQUENCE: 1

```
actggagagg ctcaggccag gcaaggaagg aggccaccga cctactgggc cgacggactc      60
ccacacagtt cctgagctgg tgccaggcag gtgacacctc ctgcagcccc cagcatgcgg     120
gcaggcccag gccccaccgt tacattggcc ctggtgctgg cggtgkcatg ggccatggag     180
ctcaagccca cagcaccacc catcttcact ggccggccct ttgtggtagc gtgggacgtg     240
cccacacagg actgtggccc acgcctcaag gtgccactgg acctgaatgc ctttgatgtg     300
caggcctcac ctaatgaggg ttttgtgaac cagaatatta ccatcttcta ccgcgaccgt     360
ctaggcctgt tatccacgct tcgattctgc cggaaggtct gtgcatggtg gttgtgccac     420
agaatgtcag gcctttgggc acaccggaag aatgctgcag aaacgtgtgg agcactacat     480
tcgggacaca cgagtctgac ggggctggcg gtcatcgact gggaggactg gcgacctgtg     540
tgggtgcgca actggcagga caaagatgtg tatcgccggt tatcacgcca gctagtggcc     600
agtcgtcacc ctgactggcc tccagaccgc atagtcaaac aggcacaata tgagtttgag     660
ttcgcagcac agcagttcat gctggagaca ctgcgttatg tcaaggcagt gcggccccgg     720
cacctctggg gcttctacct ctttcctgac tgctacaatc atgattatgt gcagaactgg     780
gagagctaca caggccgctg ccctgatgtt gaggtggccc gcaatgacca gctggcctgg     840
```

```
ctgtgggctg agagcacggc cctcttcccg tctgtctacc tggacgagac acttgcttcc    900
tcccgccatg gccgcaactt tgtgagcttc cgtgttcagg aggcccttcg tgtggctcgc    960
acccaccatg ccaaccatgc actcccagtc tacgtcttca cacgacccac ctacagccgc   1020
aggctcacgg ggcttagtga gatggacctc atctctacca ttggcgagag tgcggccctg   1080
ggcgcagctg tgtcatcctc tggggtgac gcggggtaca ccacaagcac ggagacctgc    1140
cagtacctca agattacct gacacggctg ctggtcccct acgtggtcaa tgtgtcctgg    1200
gccacccaat attgcagccg ggcccagtgc catggccatg ggcgctgtgt gcgccgcaac   1260
cccagtgcca gtaccttcct gcatctcagc accaacagtt tccgcctagt gcctggccat   1320
gcacctggtg aacccagct gcgacctgtg ggggagctca gttgggccga cattgaccac    1380
ctgcagacac acttccgctg ccagtgtact ttggcttgag tggttagcaa tgccaatngg   1440
accataggca                                                          1450
```

<210> SEQ ID NO 2
<211> LENGTH: 434
<212> TYPE: PRT
<213> ORGANISM: Homo sapiens
<220> FEATURE:
<221> NAME/KEY: MISC_FEATURE
<222> LOCATION: (18)..(18)
<223> OTHER INFORMATION: Xaa is any amino acid

<400> SEQUENCE: 2

```
Met Arg Ala Gly Pro Gly Pro Thr Val Thr Leu Ala Leu Val Leu Ala
1               5                   10                  15

Val Xaa Trp Ala Met Glu Leu Lys Pro Thr Ala Pro Pro Ile Phe Thr
            20                  25                  30

Gly Arg Pro Phe Val Val Ala Trp Asp Val Pro Thr Gln Asp Cys Gly
        35                  40                  45

Pro Arg Leu Lys Val Pro Leu Asp Leu Asn Ala Phe Asp Val Gln Ala
    50                  55                  60

Ser Pro Asn Glu Gly Phe Val Asn Gln Asn Ile Thr Ile Phe Tyr Arg
65                  70                  75                  80

Asp Arg Leu Gly Leu Leu Ser Thr Leu Arg Phe Cys Arg Lys Val Cys
                85                  90                  95

Ala Trp Trp Leu Cys His Arg Met Ser Gly Leu Trp Ala His Arg Lys
            100                 105                 110

Asn Ala Ala Glu Thr Cys Gly Ala Leu His Ser Gly His Thr Ser Leu
        115                 120                 125

Thr Gly Leu Ala Val Ile Asp Trp Glu Asp Trp Arg Pro Val Trp Val
    130                 135                 140

Arg Asn Trp Gln Asp Lys Asp Val Tyr Arg Arg Leu Ser Arg Gln Leu
145                 150                 155                 160

Val Ala Ser Arg His Pro Asp Trp Pro Pro Asp Arg Ile Val Lys Gln
                165                 170                 175

Ala Gln Tyr Glu Phe Glu Phe Ala Ala Gln Gln Phe Met Leu Glu Thr
            180                 185                 190

Leu Arg Tyr Val Lys Ala Val Arg Pro Arg His Leu Trp Gly Phe Tyr
        195                 200                 205

Leu Phe Pro Asp Cys Tyr Asn His Asp Tyr Val Gln Asn Trp Glu Ser
    210                 215                 220

Tyr Thr Gly Arg Cys Pro Asp Val Glu Val Ala Arg Asn Asp Gln Leu
225                 230                 235                 240
```

```
Ala Trp Leu Trp Ala Glu Ser Thr Ala Leu Phe Pro Ser Val Tyr Leu
            245                 250                 255

Asp Glu Thr Leu Ala Ser Ser Arg His Gly Arg Asn Phe Val Ser Phe
            260                 265                 270

Arg Val Gln Glu Ala Leu Arg Val Ala Arg Thr His His Ala Asn His
            275                 280                 285

Ala Leu Pro Val Tyr Val Phe Thr Arg Pro Thr Tyr Ser Arg Arg Leu
    290                 295                 300

Thr Gly Leu Ser Glu Met Asp Leu Ile Ser Thr Ile Gly Glu Ser Ala
305                 310                 315                 320

Ala Leu Gly Ala Ala Gly Val Ile Leu Trp Gly Asp Ala Gly Tyr Thr
            325                 330                 335

Thr Ser Thr Glu Thr Cys Gln Tyr Leu Lys Asp Tyr Leu Thr Arg Leu
            340                 345                 350

Leu Val Pro Tyr Val Val Asn Val Ser Trp Ala Thr Gln Tyr Cys Ser
            355                 360                 365

Arg Ala Gln Cys His Gly His Gly Arg Cys Val Arg Arg Asn Pro Ser
    370                 375                 380

Ala Ser Thr Phe Leu His Leu Ser Thr Asn Ser Phe Arg Leu Val Pro
385                 390                 395                 400

Gly His Ala Pro Gly Glu Pro Gln Leu Arg Pro Val Gly Glu Leu Ser
            405                 410                 415

Trp Ala Asp Ile Asp His Leu Gln Thr His Phe Arg Cys Gln Cys Thr
            420                 425                 430

Leu Ala
```